(12) United States Patent
Funk et al.

(10) Patent No.: US 7,211,579 B2
(45) Date of Patent: May 1, 2007

(54) NK-1 RECEPTOR ANTAGONISTS

(75) Inventors: Christoph Funk, Bottmingen (CH); Torsten Hoffmann, Weil am Rhein (DE); Andreas Koblet, Bottmingen (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 11/376,042

(22) Filed: Mar. 15, 2006

(65) Prior Publication Data

US 2006/0217393 A1   Sep. 28, 2006

(30) Foreign Application Priority Data

Mar. 23, 2005   (EP)   ................... 05102359

(51) Int. Cl.
*A61K 31/496* (2006.01)
*C07D 213/75* (2006.01)
*C07D 401/04* (2006.01)

(52) U.S. Cl. .................. 514/253.01; 544/360

(58) Field of Classification Search ............ None
See application file for complete search history.

(56) References Cited

U.S. PATENT DOCUMENTS

| 5,972,938 | A | 10/1999 | Rupniak et al. | |
| 6,479,482 | B2 * | 11/2002 | Bos et al. | 514/227.8 |
| 6,593,472 | B2 * | 7/2003 | Hoffmann et al. | 544/131 |
| 2003/0083345 | A1 * | 5/2003 | Hoffmann et al. | 514/318 |
| 2005/0090533 | A1 * | 4/2005 | Hoffmann et al. | 514/352 |

FOREIGN PATENT DOCUMENTS

| DE | 10008042 | 8/2000 |
| EP | 1 035 115 | 9/2000 |
| EP | 1 103 545 | 5/2001 |
| WO | WO 95/16679 | 6/1995 |
| WO | WO 95/18124 | 7/1995 |
| WO | WO 95/23798 | 9/1995 |
| WO | WO 2005/002577 A1 * | 1/2005 |

OTHER PUBLICATIONS

Barker, R., Reviews in the Neuroscieces, vol. 7, pp. 187-214 (1996).
Longmore, et al., Can. J. Physiol. Pharmacol. vol. 75, pp. 612-621 (1997).
Kramer, et al., Science, vol. 281, pp. 1640-1645 (1998).
Maggi, et al., J. Auton. Pharmacol. vol. 13, pp. 23-93 (1993).
Navari, et al., The New England Journal of Medicine, vol. 340, No. 3, pp. 190-195 (1999).
Halliwell et al., Toxicologic Pathology, vol. 25(1), pp. 53-60 (1997).
Lullmann, et al., Biochemical Pharmacology, vol. 27, pp. 1103-1108 (1978).

* cited by examiner

*Primary Examiner*—Emily Bernhardt
(74) *Attorney, Agent, or Firm*—George W. Johnston; Patricia S. Rocha-Tramaloni; Kimberly J. Prior

(57) ABSTRACT

The present invention relates to compounds of formula I

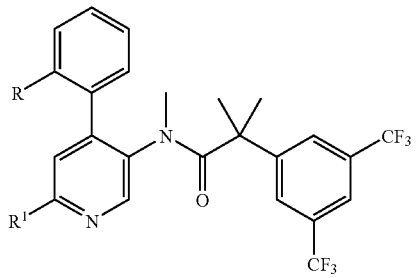

wherein
R is methyl; and
$R^1$ is 4-methyl-4-oxy-piperazin-1-yl; or
R is $CH_2OH$ and
$R^1$ is 4-methyl-piperazin-1-yl or is 4-methyl-4-oxy-piperazin-1-yl;
and to pharmaceutically acceptable acid addition salts thereof for the treatment of NK-1 receptor related diseases, for example depression, Parkinson's disease, Alzheimer's disease, anxiety, emesis, and pain.

5 Claims, No Drawings

NK-1 RECEPTOR ANTAGONISTS

PRIORITY TO RELATED APPLICATIONS

This application claims the benefit of European Application No. 05102359.6, filed Mar. 23, 2005, which is hereby incorporated by reference in its entirety.

BACKGROUND OF THE INVENTION

Substance P is a naturally occurring undecapeptide belonging to the tachykinin family of peptides, the latter being so-named because of their prompt contractile action on extravascular smooth muscle tissue. The receptor for substance P is a member of the superfamily of G protein-coupled receptors.

The neuropeptide receptor for substance P (NK-1) is widely distributed throughout the mammalian nervous system (especially brain and spinal ganglia), the circulatory system and peripheral tissues (especially the duodenum and jejunum) and are involved in regulating a number of diverse biological processes.

The central and peripheral actions of the mammalian tachykinin substance P have been associated with numerous inflammatory conditions including migraine, rheumatoid arthritis, asthma, and inflammatory bowel disease as well as mediation of the emetic reflex and the modulation of central nervous system (CNS) disorders such as Parkinson's disease (Neurosci. Res., 1996, 7, 187–214), anxiety (Can. J. Phys., 1997, 75, 612–621) and depression (Science, 1998, 281, 1640–1645).

Evidence for the usefulness of tachykinin receptor antagonists in pain, headache, especially migraine, Alzheimer's disease, multiple sclerosis, attenuation of morphine withdrawal, cardiovascular changes, oedema, such as oedema caused by thermal injury, chronic inflammatory diseases such as rheumatoid arthritis, asthma/bronchial hyperreactivity and other respiratory diseases including allergic rhinitis, inflammatory diseases of the gut including ulcerative colitis and Crohn's disease, ocular injury and ocular inflammatory diseases reviewed in "Tachykinin Receptor and Tachykinin Receptor Antagonists", J. Auton. Pharmacol., 13, 23–93, 1993.

Furthermore, Neurokinin 1 receptor antagonists are being developed for the treatment of a number of physiological disorders associated with an excess or imbalance of tachykinin, in particular substance P. Examples of conditions in which substance P has been implicated include disorders of the central nervous system such as anxiety, depression and psychosis (WO 95/16679, WO 95/18124 and WO 95/23798).

The neurokinin-1 receptor antagonists are further useful for the treatment of motion sickness and for treatment induced vomiting.

In addition, in The New England Journal of Medicine, Vol. 340, No. 3 190–195, 1999 has been described the reduction of cisplatin-induced emesis by a selective neurokinin-1-receptor antagonist.

Furthermore, U.S. Pat. No. 5,972,938 describes a method for treating a psychoimmunologic or a psychosomatic disorder by administration of a tachykinin receptor, such as NK-1 receptor antagonist.

SUMMARY OF THE INVENTION

The present invention provides compounds of formula

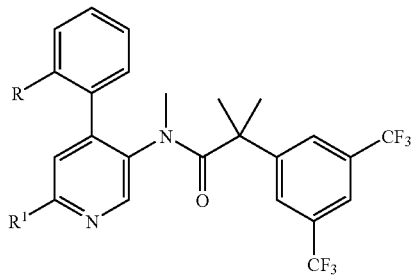

I wherein
R is methyl; and
$R^1$ is 4-methyl-4-oxy-piperazin-1-yl; or
R is $CH_2OH$ and
$R^1$ is 4-methyl-piperazin-1-yl or is 4-methyl-4-oxy-piperazin-1-yl;

and pharmaceutically acceptable acid addition salts thereof.

The invention also provides pharmaceutical compositions containing compounds of the invention and a pharmaceutical carrier. The invention further provides processes for the preparation of compounds and compositions of the invention.

The compounds of the invention have valuable therapeutic properties. They are antagonists of the Neurokinin 1 (NK-1, substance P) receptor.

Preferred indications in accordance with the present invention are those of the central nervous system, for example the treatment of certain depressive disorders or emesis. A major depressive episode is defined as being a period of at least two weeks during which, for most of the day and nearly every day, there is either depressed mood or the loss of interest or pleasure in all, or nearly all, activities.

DETAILED DESCRIPTION OF THE INVENTION

The term "pharmaceutically acceptable," such as pharmaceutically acceptable carrier, excipient, etc. means pharmacologically acceptable and substantially non-toxic to the subject to which the particular compound is administered.

The term "pharmaceutically acceptable acid addition salts" embraces salts with inorganic and organic acids, such as hydrochloric acid, nitric acid, sulfuric acid, phosphonic acid, citric acid, formic acid, fumaric acid, maleic acid, acetic acid, succinic acid, tartaric acid, methanesulfonic acid, p-toluenesulfonic acid and the like.

The term "therapeutically effective amount" means an amount that is effective to prevent, alleviate or ameliorate symptoms of disease or prolong the survival of the subject being treated.

The present invention provides compounds of formula

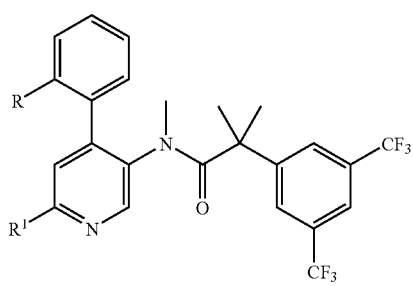

I wherein
R is methyl; and
R¹ is 4-methyl-4-oxy-piperazin-1-yl; or
R is CH₂OH and
R¹ is 4-methyl-piperazin-1-yl or is 4-methyl-4-oxy-piperazin-1-yl;

and pharmaceutically acceptable acid addition salts thereof.

The present invention provides compounds of formula I, which include

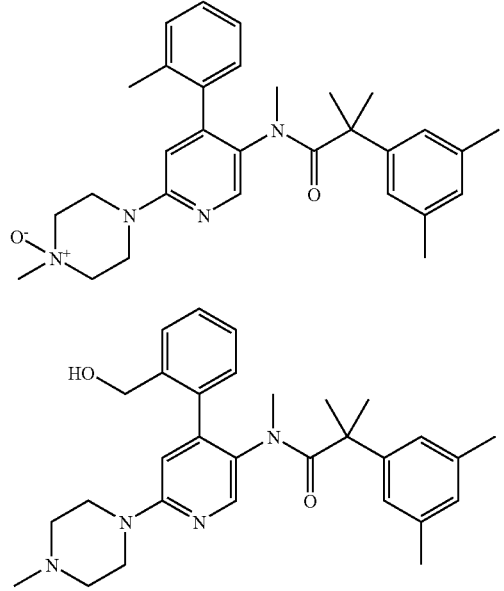

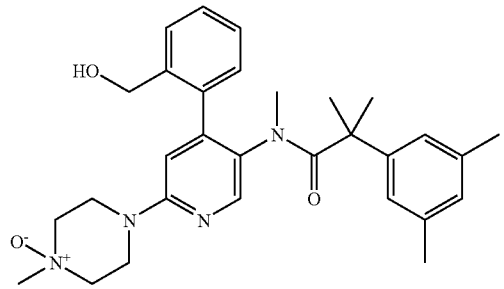

2-(3,5-bis-trifluoromethyl-phenyl)-N-methyl-N-[6-(4-methyl-4-oxy-piperazin-1-yl)-4-o-tolyl-pyridin-3-yl]-isobutyramide (compound I-1);
2-(3,5-bis-trifluoromethyl-phenyl)-N-[4-(2-hydroxymethyl-phenyl)-6-(4-methyl-piperazin-1-yl)-pyridin-3-yl]-N-methyl-isobutyramide (compound I-2); and
2-(3,5-dimethyl-phenyl)-N-[4-(2-hydroxymethyl-phenyl)-6-(4-methyl-4-oxy-piperazin-1-yl)-pyridin-3-yl]-N-methyl-isobutyramide (1-3), and pharmaceutically acceptable salts thereof.

Preferred are compounds of formulas I-1 and I-2. These compounds have an improved solubility with regard to similar compounds, described in EP 1 035 115 A1 or EP 1 103 545 A1.

The present compounds of formula I and their pharmaceutically acceptable salts can be prepared by methods known in the art, for example, by processes described below, which processes comprise a) reacting a compound of formula

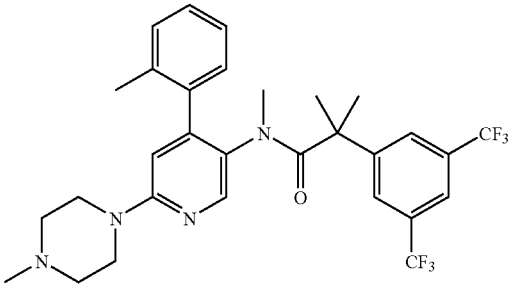

with OXONE® [(potassium peroxymonosulfate) 2KHSO₅.KHSO₄.K₂SO₄]
to obtain a compound of formula

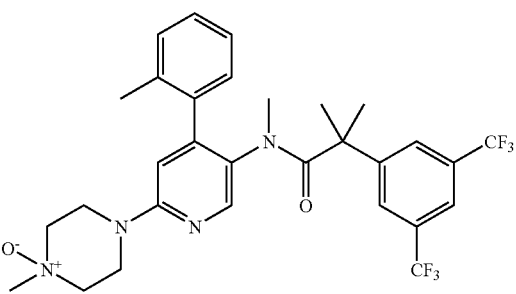

or
b) reacting a compound of formula

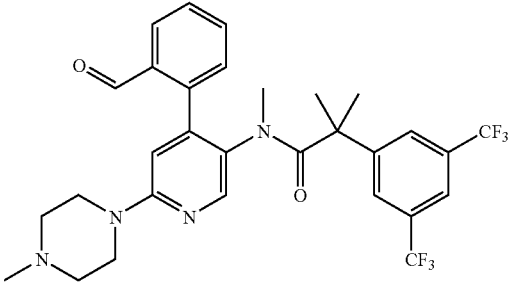

with NaBH₄
to obtain a compound of formula

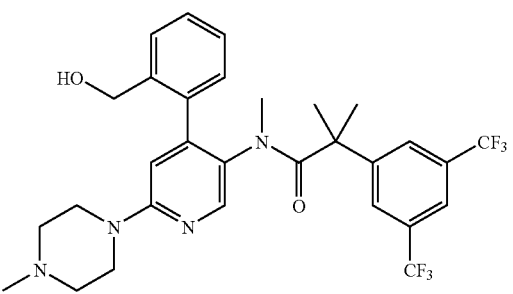

and
if desired, converting the compound obtained into a pharmaceutically acceptable acid addition salt thereof.

The salt formation is effected at room temperature in accordance with methods which are known per se and which are familiar to any person skilled in the art. Not only salts with inorganic acids but also salts with organic acids are contemplated. Hydrochlorides, hydrobromides, sulphates, nitrates, citrates, acetates, maleates, succinates, methansulphonates, p-toluenesulphonates and the like are examples of such salts.

The following schemes 1 and 2 describe the processes for preparation of compounds of formula I in more detail. The starting materials of formulae IV and II are known compounds and may be prepared according to methods known in the art.

In the schemes the following abbreviations have been used:
DIPEA N-ethyldiisopropyl-amine
KHMDS potassium hexamethyldisilazide Scheme 1

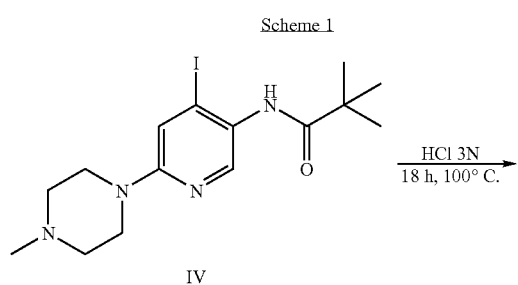

IV

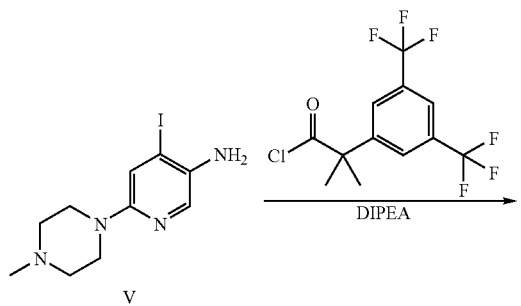

V

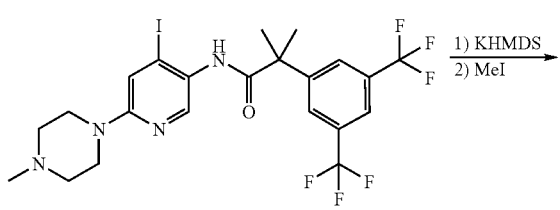

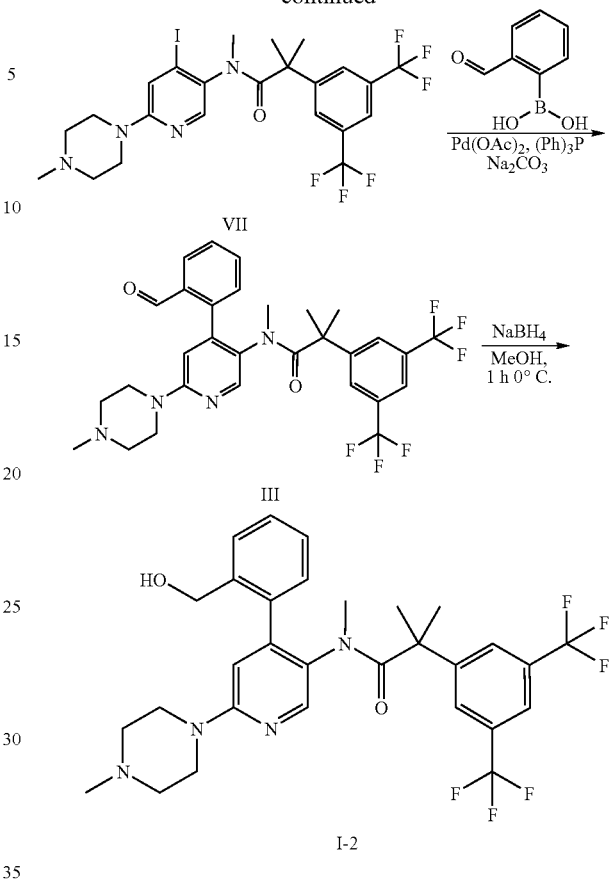

A mixture of N-[4-iodo-6-(4-methyl-piperazin-1-yl)-pyridin-3-yl]-2,2-dimethylpropionamide (IV) (synthesis described in DE10008042) in hydrochloric acid is stirred for about 18 h at 100° C. After cooling to 0° C., the reaction mixture is purified and dried in conventional manner. Then to a suspension of 4-iodo-6-(4-methyl-piperazin-1-yl)-pyridin-3-ylamine (V) and N,N-diisopropyl ethyl amine in dichloromethane is added 2-(3,5-bis-trifluoromethyl-phenyl)-2-methyl-propionyl chloride at 0° C. The reaction mixture is stirred for about 2 h at room temperature and 2 h at reflux. After cooling to room temperature, the reaction mixture is washed and dried, and a solution of 2-(3,5-bis-trifluoromethyl-phenyl)-N-[4-iodo-6-(4-methylpiperazin-1-yl)-pyridin-3-yl]-isobutyramide (VI) in N,N-dimethylformamide is added at 0° C. to a solution of potassium bis(trimethylsilyl)amide in tetrahydrofuran. After stirring at 0° C., iodomethane is added. The mixture is stirred for 2 days in a closed flask. The reaction mixture is concentrated and purified.

A mixture of the obtained 2-(3,5-bis-trifluoromethyl-phenyl)-N-[4-iodo-6-(4-methylpiperazin-1-yl)-pyridin-3-yl]-N-methyl-isobutyramide (VII), aqueous sodium carbonate solution, palladium(II) acetate, triphenylphosphine and 2-formylphenylboronic acid in dimethoxyethane is evacuated and filled with argon and stirred for about 2 h at 80° C. After cooling to room temperature, the reaction mixture is diluted, washed and dried.

Then, to a mixture of sodium borohydride in methanol is added at 0° C. 2-(3,5-bis-trifluoromethyl-phenyl)-N-[4-(2-formyl-phenyl)-6-(4-methyl-piperazin-1-yl)-pyridin-3-yl]-N-methyl-isobutyramide (III). After stirring at 0° C. for 1 h brine is added at 0° C. The mixture is stirred for about 30 min, dried and purified to obtain a compound of formula I-2.

Scheme 2

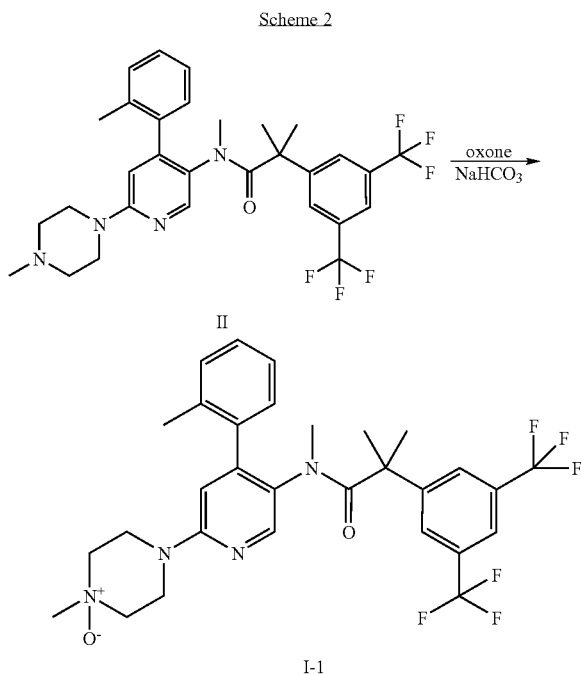

To a solution of 2-(3,5-bis-trifluoromethyl-phenyl)-N-methyl-N-[6-(4-methyl-piperazin-1-yl)-4-o-tolyl-pyridin-3-yl]-isobutyramide (II) (synthesis described in DE10008042) and sodium hydrogen carbonate in methanol and water are added potassium monopersulfate triple salt at room temperature. After stirring for about 6 h the reaction mixture is concentrated and purified to obtain a compound of formula I-1.

As mentioned earlier, the compounds of formula I and their pharmaceutically usable addition salts possess valuable pharmacological properties. The compounds of the present invention are antagonists of the Neurokinin 1 (NK-1, substance P) receptor.

The compounds were investigated in accordance with the tests given hereinafter. The affinity of test compounds for the $NK_1$ receptor was evaluated at human $NK_1$ receptors in CHO cells infected with the human $NK_1$ receptor (using the Semliki virus expression system) and radiolabelled with [$^3$H]substance P (final concentration 0.6 nM). Binding assays were performed in HEPES buffer (50 mM, pH 7.4) containing BSA (0.04%) leupeptin (8 μg/ml), $MnCl_2$ (3 mM) and phosphoramidon (2 μM). Binding assays consisted of 250 μl of membrane suspension ($1.25 \times 10^5$ cells/assay tube), 0.125 μl of buffer of displacing agent and 125 μl of [$^3$H] substance P. Displacement curves were determined with at least seven concentrations of the compound. The assay tubes were incubated for 60 min at room temperature after which time the tube contents were rapidly filtered under vacuum through GF/C filters presoaked for 60 min with PEI (0.3%) with 2×2 ml washes of HEPES buffer (50 mM, pH 7.4). The radioactivity retained on the filters was measured by scintillation counting. All assays were performed in triplicate in at least 2 separate experiments.

The affinity to the NK-1 receptor, given as pKi is described in the table below:

| | |
|---|---|
| 2-(3,5-bis-trifluoromethyl-phenyl)-N-methyl-N-[6-(4-methyl-4-oxy-piperazin-1-yl)-4-o-tolyl-pyridin-3-yl]-isobutyramide (compound I-1) | 9.0 |
| 2-(3,5-bis-trifluoromethyl-phenyl)-N-[4-(2-hydroxymethyl-phenyl)-6-(4-methyl-piperazin-1-yl)-pyridin-3-yl]-N-methyl-isobutyramide (compound I-2) | 9.1 |

In addition to their good affinity to the NK-1 receptor, compounds of formulas I-1 and I-2 possess advantageous pharmaceutical properties. For example, the compound of formula I-2 shows a very good solubility and permeability when compared with structurally-related compounds disclosed in the prior art (EP 1 035 115). The following results are provided:

Solubility

Method Description Equilibrium Solubility

Equilibrium solubility values were determined at pH 4.2 (0.15 M Citrat-buffer). A known amount of drug, generally 1–2 mg, was added to 250 μl of buffer (glass tubes), and the resulting suspension was stirred for 2 h (21° C.), after 5 minutes of sonification. The pH of the solution was checked and corrected if necessary (in case of pH correction, the solution was once more shaken and equilibrated), and after 24 h the suspension was filtered through a 0.65-μm filter. The filtered solution was then assayed by HPLC to determine the drug concentration. In cases where the drug had completely dissolved in the buffer, the value for equilibrium solubility was assumed to be higher than the value determined by HPLC and was reported as such. Stock solutions (~1 mg/ml) in DMSO were used in the preparation of a calibration curve in the related buffer using HPLC analytics.

Results

| Compound | Solubility (μg/mL) | pH | Example |
|---|---|---|---|
| 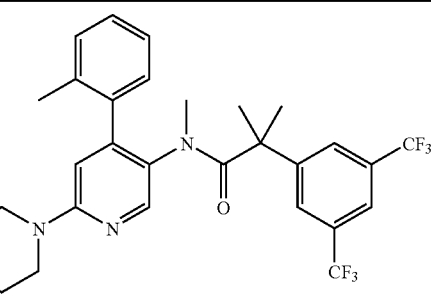 | 1 | 6.5 buffer: 0.05 M Phosphate | EP 1 035 115 |

Results

| Compound | Solubility (μg/mL) | pH | Example |
|---|---|---|---|
| (structure: 2-(hydroxymethyl)phenyl pyridine with N-methylpiperazine, N-methyl amide, 3,5-bis(trifluoromethyl)phenyl) | 8 | 6.7 buffer: 0.05 M Phosphate | Compound I-2 |
| (structure: 2-methylphenyl pyridine with N-methylpiperazine, N-methyl amide, 3,5-bis(trifluoromethyl)phenyl) | 26 | 4.1 buffer: 0.15 M Citrate | EP 1 035 115 |
| (structure: 2-(hydroxymethyl)phenyl pyridine with N-methylpiperazine, N-methyl amide, 3,5-bis(trifluoromethyl)phenyl) | 200 | 4.1 buffer: 0.15 M Citrate | Compound I-2 |

The solubility of the present compound I-2 is 8-fold higher than the compared compound disclosed in EP 1035 115.

Permeability

Method Description:

The permeability has been searched by the PAMPA PSR4p assay, which is based on 96 well microplates. The permeability is measured using a "sandwich" construction. A filterplate is coated with phospholipids (membrane) and placed into a donor plate containing a drug/buffer solution. Finally the filterplate is filled with buffer solution (acceptor). The donor concentration is measured at t-start (reference) and compared with the donor and acceptor concentration after a certain time t-end.

The following setup is used for the PAMPA PSR4p assay:

Donor: 0.05 M MOPSO buffer at ph 6.5+0.5% (w/v) Glyco cholic acid

Membrane: 10% (w/v) Egg lecithin+0.5% (w/v) cholesterol in dodecane

Acceptor: 0.05 MOPSO buffer at pH 6.5

The liquid handling is done with a TECAN RSP150 pipetting robot. The drug analysis is based on UV spectroscopy. All samples are transferred into 96 well UV plates. A SpectralMax 190 UV plate reader is used to collect the UV spectras.

The pipetting steps can be divided into four parts: 1. Dilution of stock solutions and filtration, 2. Preparation of reference and PAMPA PSR4p sandwich, 3. Transfer of acceptor solutions into UV plate, 4. Transfer of donor solutions into UV plate. The PAMPA PSR4p assay contains information about the sample precipitation in the donor buffer UV spectras of the sample, read at the start of the assay (t-start: reference) and at the end (t-end: donor, acceptor) allow the determination of a sample distribution in donor, membrane and acceptor. Because of the known permeation time (t-end, t-start) a permeation constant can be retrieved. The unit of this constant is $10^{-6}$ cm/s, indicating that this is a kinetic value or in other words the permeation speed.

Results

| Example | Structure | PE (cm/s × $10^{-6}$) | Acceptor | Membrane | Donor | pH | Stock solution |
|---|---|---|---|---|---|---|---|
| EP 1 035 115 | 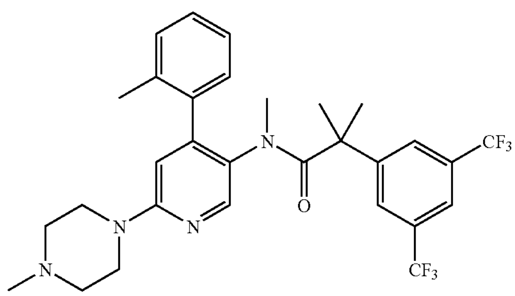 | 0.56 class: medium | 2 | 49 | 50 | 6.5 | DMSO |
| I-2 | 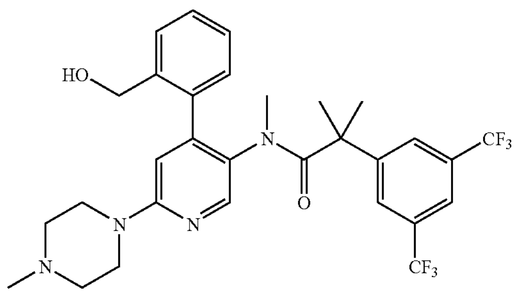 | 1.81 class: high | 3 | 72 | 26 | 6.5 | DMSO |

It can be said that the permeation speed is three times higher of compound I-2, when compared with the corresponding compound, disclosed in EP 1 035 115.

Furthermore, 2-(3,5-bis-trifluoromethyl-phenyl)-N-methyl-N-[6-(4-methyl-piperazin-1-yl)-4-o-tolyl-pyridin-3-yl]-isobutyramide (EP 1 035 115) has the potential to produce phospholipidoses (toxic effect) due to the fact that it contains a basic nitrogen atom, which may protonate under physiological conditions. The advantage for the present compound of formula I-1 is that the N-oxide is neutral and has therefore no potential to produce phospholipidoses (Halliwell W H, Cationic amphiphilic drug-induced phospholipidosis, Toxicologic Pathology, 1997, 25(1), 53–60 and Lullmann H et al., Lipidosis induced by amphiphilicationic drugs, Biochem. Pharmacol., 1978, 27, 1103–1108). In addition, the N-oxide (compound of formula I-1) has a higher metabolic stability in vitro in microsomes in comparison with 2-(3,5-bis-trifluoromethyl-phenyl)-N-methyl-N-[6-(4-methyl-piperazin-1-yl)-4-o-tolyl-pyridin-3-yl]-isobutyramide.

The present invention also provides pharmaceutical compositions containing compounds of the invention or pharmaceutically acceptable salts thereof and a pharmaceutically acceptable carrier. Such pharmaceutical compositions can be in the form of tablets, coated tablets, dragées, hard and soft gelatin capsules, solutions, emulsions or suspensions. The pharmaceutical compositions also can be in the form of suppositories or injectable solutions.

The pharmaceutical compositions of the invention, in addition to one or more compounds of the invention, contain a pharmaceutically acceptable carrier. Suitable pharmaceutically acceptable carriers include pharmaceutically inert, inorganic or organic carriers. Lactose, corn starch or derivatives thereof, talc, stearic acid or its salts etc can be used as such excipients e.g. for tablets, dragées and hard gelatine capsules.

Suitable excipients for soft gelatine capsules are e.g. vegetable oils, waxes, fats, semi-solid and liquid polyols etc.

Suitable excipients for the manufacture of solutions and syrups are e.g. water, polyols, saccharose, invert sugar, glucose etc.

Suitable excipients for injection solutions are e.g. water, alcohols, polyols, glycerol, vegetable oils etc.

Suitable excipients for suppositories are e.g. natural or hardened oils, waxes, fats, semi-liquid or liquid polyols etc.

Moreover, the pharmaceutical compositions can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The present invention also provides a method for the manufacture of pharmaceutical compositions. Such process comprises bringing one or more compounds of formula I and/or pharmaceutically acceptable acid addition salts thereof and, if desired, one or more other therapeutically valuable substances into a galenical administration form together with one or more therapeutically inert carriers.

The compounds and compositions of the present invention can be administered in a conventional manner, for example, orally, rectally, or parenterally. The pharmaceutical compositions of the invention can be administered orally, for example, in the form of tablets, coated tablets, dragées, hard and soft gelatin capsules, solutions, emulsions, or suspensions. The pharmaceutical compositions also can be administered rectally, for example, in the form of suppositories, or parenterally, for example, in the form of injectable solutions.

Compounds of the present invention are NK-1 receptor antagonists. The present invention also provides methods of treating disorders selected from the group consisting of migraines, rheumatoid arthritis, asthma, emesis, Parkinson's disease, pain, headaches, Alzheimer's disease, anxiety, depression, multiple sclerosis, attenuation of morphine withdrawal, cardiovascular disorders, oedema, Crohn's disease, allergic rhinitis, psychosis, motion sickness, and vomiting which comprises administering to an individual a therapeutically effective amount of a compound of formula I.

The dosage at which compounds of the invention can be administered can vary within wide limits and will, of course, be fitted to the individual requirements in each particular case. In general, in the case of oral administration a daily dosage of about 10 to 1000 mg per person of a compound of general formula I should be appropriate, although the above upper limit can also be exceeded when necessary.

The following Examples illustrate the present invention without limiting it. All temperatures are given in degrees Celsius.

EXAMPLE A

Tablets of the following composition are manufactured in the usual manner:

|  | mg/tablet |
|---|---|
| Active substance | 5 |
| Lactose | 45 |
| Corn starch | 15 |
| Microcrystalline cellulose | 34 |
| Magnesium stearate | 1 |
| Tablet weight | 100 |

EXAMPLE B

Capsules of the following composition are manufactured:

|  | mg/capsule |
|---|---|
| Active substance | 10 |
| Lactose | 155 |
| Corn starch | 30 |
| Talc | 5 |
| Capsule fill weight | 200 |

The active substance, lactose and corn starch are firstly mixed in a mixer and then in a comminuting machine. The mixture is returned to the mixer, the talc is added thereto and mixed thoroughly. The mixture is filled by machine into hard gelatine capsules.

EXAMPLE C

Suppositories of the following composition are manufactured:

|  | mg/supp. |
|---|---|
| Active substance | 15 |
| Suppository mass | 1285 |
| Total | 1300 |

The suppository mass is melted in a glass or steel vessel, mixed thoroughly and cooled to 45° C. Thereupon, the finely powdered active substance is added thereto and stirred until it has dispersed completely. The mixture is poured into suppository moulds of suitable size, left to cool, the suppositories are then removed from the moulds and packed individually in wax paper or metal foil.

EXAMPLE 1

2-(3,5-Bis-trifluoromethyl-phenyl)-N-methyl-N-[6-(4-methyl-4-oxy-piperazin-1-yl)-4-o-tolyl-pyridin-3-yl]-isobutyramide (compound I-1)

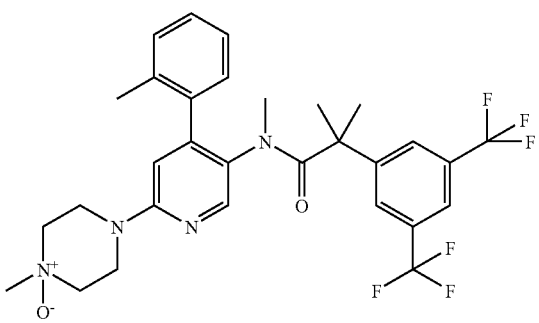

To a solution of 2.00 g (3.46 mmol) 2-(3,5-bis-trifluoromethyl-phenyl)-N-methyl-N-[6-(4-methyl-piperazin-1-yl)-4-o-tolyl-pyridin-3-yl]-isobutyramide (synthesis described in DE10008042) and 610 mg (7.26 mmol) sodium hydrogen carbonate in 40 ml methanol and 8 ml water were added 1.10 g (1.80 mmol) potassium monopersulfate triple salt at room temperature during 15 minutes. After stirring for 6 h at room temperature the reaction mixture was concentrated in vacuo and purified by flash chromatography to give 1.65 g (80%) of the title compound as white crystals.

MS m/e (%): 595 (M+H$^+$, 100)

EXAMPLE 2

2-(3,5-Bis-trifluoromethyl-phenyl)-N-[4-(2-hydroxymethyl-phenyl)-6-(4-methyl-piperazin-1-yl)-pyridin-3-yl]-N-methyl-isobutyramide (compound I-2)

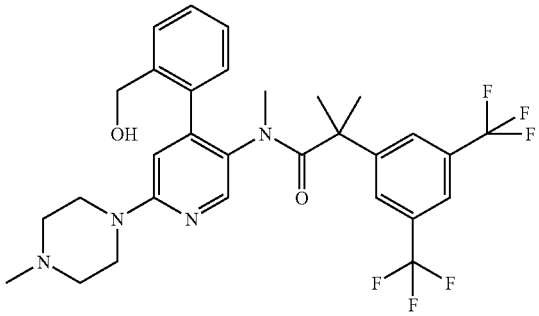

4-Iodo-6-(4-methyl-piperazin-1-yl)-pyridin-3-ylamine (compound V)

A mixture of 2.20 g (5.47 mmol) N-[4-iodo-6-(4-methyl-piperazin-1-yl)-pyridin-3-yl]-2,2-dimethyl-propionamide (synthesis described in DE10008042) in 50 ml 3 N hydrochloric acid was stirred for 18 h at 100° C. After cooling to 0° C. the reaction mixture was washed twice with ether (50 ml). The aqueous phase was treated with 50 ml dichloromethane and basified with a 1 M solution of sodium carbonate. The organic phase was separated and the aqueous phase was extracted four times with 50 ml dichloromethane. The combined organic layers were dried over sodium sulfate and concentrated in vacuo to give 1.60 g (92%) of the title compound as an off-white solid.

MS m/e (%): 319 (M+H+, 100)

2-(3,5-Bis-trifluoromethyl-phenyl)-N-[4-iodo-6-(4-methyl-piperazin-1-yl)-pyridin-3-yl]-isobutyramide (compound VI)

To a suspension of 1.60 g (5.03 mmol) 4-iodo-6-(4-methyl-piperazin-1-yl)-pyridin-3-ylamine and 975 mg (7.54 mmol) N,N-diisopropyl ethyl amine in 16 ml dichloromethane was added dropwise 1.76 g (5.53 mmol) 2-(3,5-bis-trifluoromethyl-phenyl)-2-methyl-propionyl chloride at 0° C. The reaction mixture was stirred for 2 h at room temperature and 2 h at reflux. After cooling to room temperature the reaction mixture was washed with 20 ml of a 1 M aqueous sodium carbonate solution and 20 ml water. The combined organic layers were dried over sodium sulfate and concentrated in vacuo to give 3.39 g (100%) of the crude title compound as a brown oil.

MS m/e (%): 601 (M+H+, 100)

2-(3,5-Bis-trifluoromethyl-phenyl)-N-[4-iodo-6-(4-methyl-piperazin-1-yl)-pyridin-3-yl]-N-methyl-isobutyramide (compound VII)

To a solution of 3.09 g (5.15 mmol) 2-(3,5-bis-trifluoromethyl-phenyl)-N-[4-iodo-6-(4-methyl-piperazin-1-yl)-pyridin-3-yl]-isobutyramide in 30 ml N,N-dimethylformamide were added at 0° C. 6.8 ml (6.2 mmol) of a 0.91 M solution of potassium bis(trimethylsilyl)amide in tetrahydrofuran. After stirring at 0° C. for 40 min 0.352 ml (5.66 mmol) iodomethane were added. The mixture was stirred for 2 days in a closed flask. The reaction mixture was concentrated in vacuo and purified by flash chromatography to give 980 mg (31%) of the title compound as a brown oil.

MS m/e (%): 615 (M+H+, 100)

2-(3,5-Bis-trifluoromethyl-phenyl)-N-[4-(2-formyl-phenyl)-6-(4-methyl-piperazin-1-yl)-pyridin-1-yl)-3-yl]-N-methyl-isobutyramide (compound III)

A mixture of 900 mg (1.47 mmol) 2-(3,5-bis-trifluoromethyl-phenyl)-N-[4-iodo-6-(4-methyl-piperazin-1-yl)-pyridin-3-yl]-N-methyl-isobutyramide, 2.8 ml of a 1 M aqueous sodium carbonate solution, 33 mg (0.15 mmol) palladium (II) acetate, 77 mg (0.29 mmol) triphenylphosphine and 242 mg (1.61 mmol) 2-formylphenylboronic acid in 5 ml dimethoxyethane was evacuated and filled with argon and stirred for 2 h at 80° C. After cooling to room temperature the reaction mixture was diluted with 20 ml ethyl acetate and washed with 20 ml brine. The combined organic layers were dried over sodium sulfate, concentrated and purified by flash chromatography to give 584 mg (67%) of the title compound as a light brown solid. MS m/e (%): 593 (M+H+, 100)

2-(3,5-Bis-trifluoromethyl-phenyl)-N-[4-(2-hydroxymethyl-phenyl)-6-(4-methyl-piperazin-1-yl)-pyridin-3-yl]-N-methyl-isobutyramide (compound I-2)

To a mixture of 15 mg (0.41 mmol) sodium borohydride in 2 ml methanol were added at 0° C. 200 mg (0.338 mmol) 2-(3,5-bis-trifluoromethyl-phenyl)-N-[4-(2-formyl-phenyl)-6-(4-methyl-piperazin-1-yl)-pyridin-3-yl]-N-methyl-isobutyramide. After stirring at 0° C. for 1 h 1 ml brine was added at 0° C. The mixture was stirred for 30 min. Methanol was distilled off and the residue was diluted with 20 ml ethyl acetate and washed with 20 ml brine. The organic layer was dried over sodium sulfate, concentrated and purified by flash chromatography to give 137 mg (68%) of the title compound as a light brown solid.

MS m/e (%): 595 (M+H+, 100)

The invention claimed is:
1. The compound 2-(3,5-bis-trifluoromethyl-phenyl)-N-methyl-N-[6-(4-methyl-4-oxy-piperazin-1-yl)-4-o-tolyl-pyridin-3-yl]-isobutyramide (I-1):

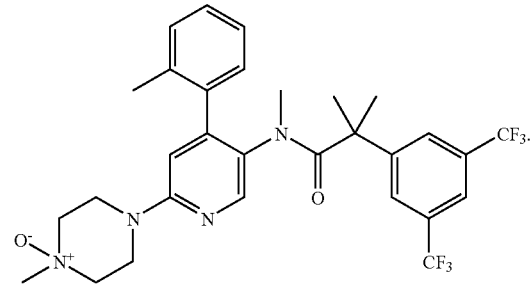

I-1

2. The compound 2-(3,5-dimethyl-phenyl)-N-[4-(2-hydroxymethyl-phenyl)-6-(4-methyl-4-oxy-piperazin-1-yl)-pyridin-3-yl]-N-methyl-isobutyramide (I-3):

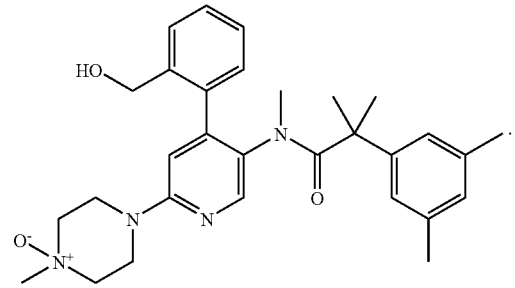

I-3

3. A pharmaceutical composition comprising a therapeutically effective amount of the compound 2-(3,5-bis-trifluoromethyl-phenyl)-N-methyl-N-[6-(4-methyl-4-oxy-piperazin-1-yl)-4-o-tolyl-pyridin-3-yl]-isobutyramide

I-1

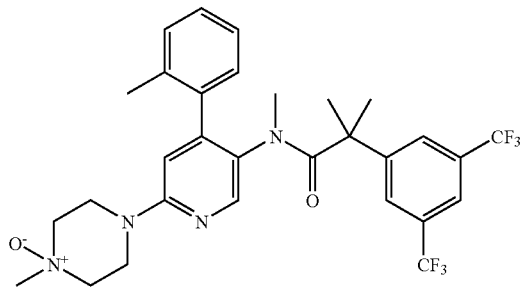

and a pharmaceutically acceptable carrier.

4. A pharmaceutical composition comprising a therapeutically effective amount of the compound 2-(3,5-dimethyl-phenyl)-N-[4-(2-hydroxymethyl-phenyl)-6-(4-methyl-4-oxy-piperazin-1-yl)-pyridin-3-yl]-N-methyl-isobutyramide

I-3

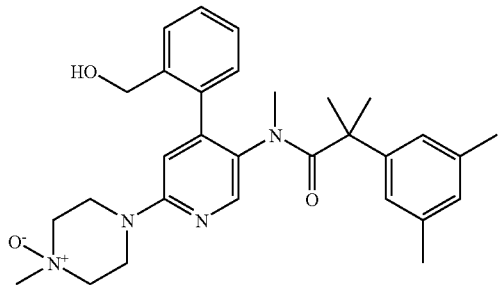

and a pharmaceutically acceptable carrier.

5. A process for preparing a compound of formula I

I

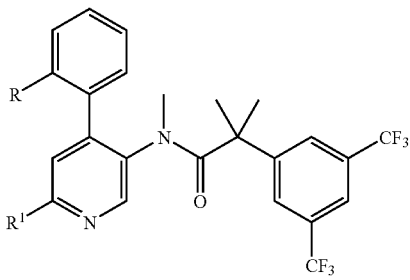

wherein
R is methyl; and
R¹ is 4-methyl-4-oxy-piperazin-1-yl; or
R is CH₂OH and
R¹ is 4-methyl-piperazin-1-yl or is 4-methyl-4-oxy-piperazin-1-yl;
or a pharmaceutically acceptable acid addition salt thereof, which process is selected from the group consisting of a) reacting a compound of formula

II

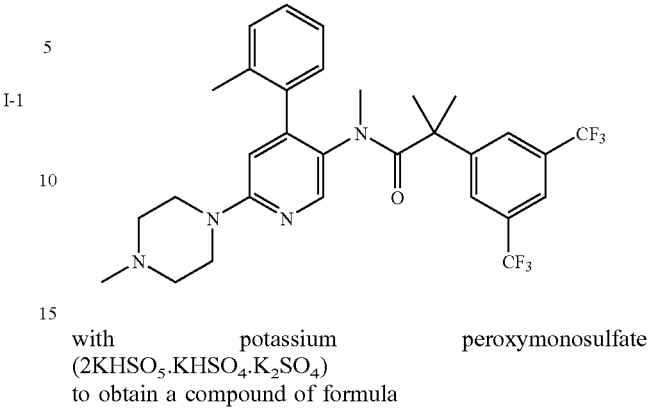

with potassium peroxymonosulfate (2KHSO₅·KHSO₄·K₂SO₄)
to obtain a compound of formula

I-1

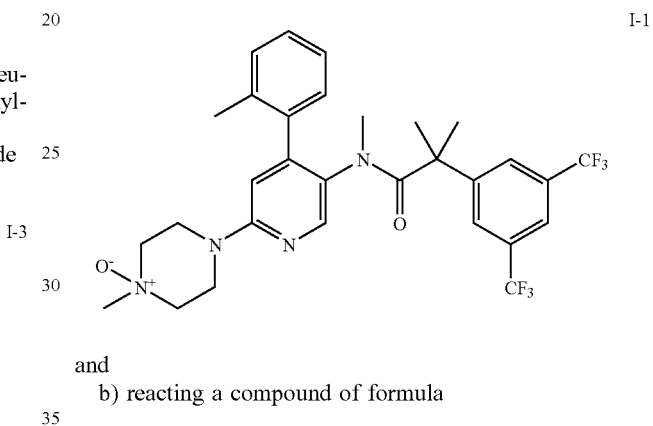

and
b) reacting a compound of formula

III

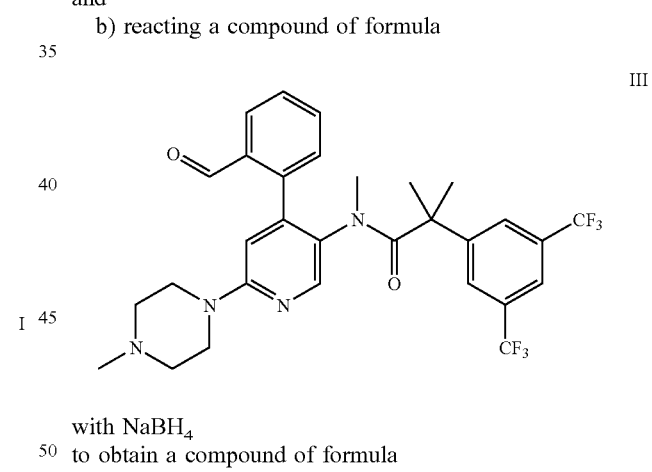

with NaBH₄
to obtain a compound of formula

I-2

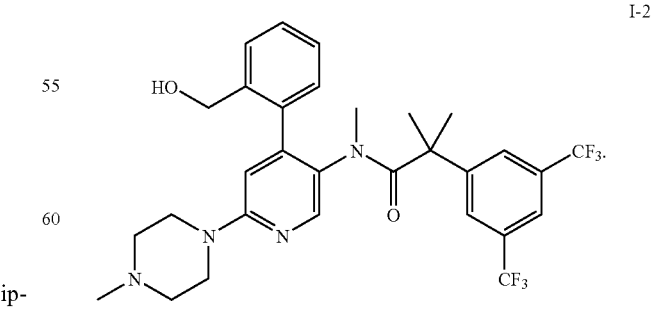

* * * * *